US012653600B2

(12) United States Patent 
Marion et al.

(10) Patent No.: US 12,653,600 B2 
(45) Date of Patent: Jun. 16, 2026

(54) BREACH DETECTION IN BIPOLAR ELECTROSURGICAL INSTRUMENT SHEATH

(71) Applicant: Intuitive Surgical Operations, Inc., Sunnyvale, CA (US)

(72) Inventors: Duane W. Marion, Scottsdale, AZ (US); Kyle W. Clements, Sunnyvale, CA (US); Zahi P. Hakim, Santa Clara, CA (US); Andrew D. Rauch, San Francisco, CA (US); Ann Yadlowsky, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1275 days.

(21) Appl. No.: 17/435,334

(22) PCT Filed: Feb. 28, 2020

(86) PCT No.: PCT/US2020/020413 
§ 371 (c)(1), 
(2) Date: Aug. 31, 2021

(87) PCT Pub. No.: WO2020/180693 
PCT Pub. Date: Sep. 10, 2020

(65) Prior Publication Data 
US 2022/0133390 A1 May 5, 2022

Related U.S. Application Data

(60) Provisional application No. 62/812,731, filed on Mar. 1, 2019.

(51) Int. Cl. 
A61B 18/12 (2006.01) 
A61B 18/14 (2006.01) 
*A61B 18/00* (2006.01)

(52) U.S. Cl. 
CPC ...... *A61B 18/1233* (2013.01); *A61B 18/1442* (2013.01); *A61B 2018/00083* (2013.01); 
(Continued)

(58) Field of Classification Search 
CPC ...... A61B 18/1233; A61B 2018/00869; A61B 2018/00827; A61B 2018/00833; 
(Continued)

(56) References Cited

U.S. PATENT DOCUMENTS 5,312,401 A * 5/1994 Newton ................. A61B 18/14 
606/42 
2009/0234353 A1* 9/2009 McPherson ........ A61B 18/1233 
606/35

(Continued)

FOREIGN PATENT DOCUMENTS

EP 0596909 A1 5/1994 
EP 2881050 A2 6/2015 
(Continued)

OTHER PUBLICATIONS

Harker, Keith. "High Voltage Power Network Construction—7.4. 1.6 Cable Dielectric Loss and Loss Angle." 2018. Institution of Engineering and Technology. pp. 159-160. (Year: 2018).* 
(Continued)

*Primary Examiner* — Linda C Dvorak 
*Assistant Examiner* — Davina E. Lee 
(74) *Attorney, Agent, or Firm* — Schwegman, Lundberg & Woessner, P.A.

(57) ABSTRACT

A system is provided to detect a breach of an insulative sheath in a bipolar electrosurgical instrument the system including: a first pulse detection circuit to detect a first high frequency (HF) signal component of a HF signal conducted on a lead of the bipolar instrument; a second pulse detection circuit to detect a second HF signal component of the HF 
(Continued)

signal conducted on a conductive shield surrounding the lead; magnitude difference sampling logic to produce sample values indicative of magnitude difference between the first HF signal component and the second HF signal component; and current detection logic to detect current flow between the shield and anatomical tissue based upon the sample values.

15 Claims, 7 Drawing Sheets

(52) U.S. Cl.
CPC ............... *A61B 2018/00607* (2013.01); *A61B 2018/00827* (2013.01); *A61B 2018/00869* (2013.01)

(58) Field of Classification Search
CPC ........... A61B 2018/00898; A61B 2018/00648; A61B 18/1442
See application file for complete search history.

(56) References Cited

U.S. PATENT DOCUMENTS

| | | | | |
|---|---|---|---|---|
| 2015/0282860 | A1* | 10/2015 | Anderson | A61B 18/1206 |
| | | | | 606/34 |
| 2018/0214195 | A1* | 8/2018 | Fraasch | A61N 1/303 |

FOREIGN PATENT DOCUMENTS

| | | |
|---|---|---|
| WO | WO-9300862 A2 | 1/1993 |
| WO | WO-2018222899 A1 | 12/2018 |

OTHER PUBLICATIONS

International Search Report and Written Opinion for Application No. PCT/US2020/020413, mailed on Jul. 24, 2020, 17 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2020/020413, mailed on Sep. 16, 2021, 10 pages.

* cited by examiner

600

604 Algorithm Program Instructions

602 Select algorithm type

606 Select algorithm parameters

608 Select comparator thresholds

610 Monitor bipolar lead and shield while bipolar ESI and monopolar ESI are active 612 Aberrant current ?
No
Yes 614 Send alert

702

704

706    (A)      (B)      (C)      (D)      (E)

708    708     708

710

Time

BREACH DETECTION IN BIPOLAR ELECTROSURGICAL INSTRUMENT SHEATH

CLAIM OF PRIORITY

This application is a U.S. National Stage Filing under 35 U.S.C. 371 from International Application No. PCT/US2020/020413, filed on Feb. 28, 2020, and published as WO 2020/180693 A1 on Sep. 10, 2020, which claims the benefit of priority to U.S. Provisional Patent Application No. 62/812,731, filed on Mar. 1, 2019, each of which is incorporated by reference herein in its entirety.

BACKGROUND

Electrosurgery involves the use of electricity to cause thermal destruction of biological tissue to cut or remove the tissue through desiccation, coagulation, or vaporization, for example. Benefits include the ability to make precise cuts with limited blood loss. Electrosurgical instruments are frequently used during surgical procedures to help prevent blood loss in hospital operating rooms or in outpatient procedures. The two types of electrosurgery most commonly used are high-frequency electrosurgery and electrocautery. High-frequency electrosurgery involves high-frequency (radio frequency) alternating current that is converted to heat by resistance as it passes through the tissue. The heat buildup within the tissue causes thermal tissue damage resulting in incision or debulking, for example. Electrocautery also involves direct transference of heat to tissue. Instead of passing electrical current through the tissue, however, the current is used to heat a handheld element, which is then applied to the tissue. Additional modalities of electrosurgery include electrolysis, which uses a chemical reaction created by direct current to damage tissue, and coblation, which uses an electrical current to ionize a conduction medium such as isotonic saline, which is then used to transmit heat to tissue.

Bipolar and monopolar are examples of two modalities for energy delivery during an electrosurgical procedure. A monopolar electrosurgical technique involves passage of current from a probe electrode, to patient tissue and through the patient tissue to a return pad to complete the electric current circuit. A bipolar electrosurgical technique typically involves current passage through only a portion of patient tissue disposed between two arms of a forceps shaped electrode. The conductive leads of a bipolar instrument are surrounded by an electrically conductive safety shield that is surrounded by the non-conducting outer insulating sheath.

During electrosurgery it is common for an active monopolar energy instrument to contact an electrode of a nearby bipolar instrument and to transmit energy to the bipolar instrument arms, particularly when the bipolar instrument can also be used for mechanical grasping. This contact can either be inadvertent or intentional, as some surgeons have been taught to "buzz" the bipolar grasper with monopolar energy to create a hemostatic effect, for example. When this occurs, the monopolar energy can travel through the bipolar instrument arms and become capacitively coupled to the shield of the bipolar instrument. If this monopolar energy is coupled to the bipolar instrument and the insulative sheath of the bipolar instrument suffers a breach, an alternate aberrant current path that includes the shield is created. A typical bipolar instrument operates at a voltage in a range of approximately 60 Vp-500 Vp, and a typical monopolar instrument operates at a voltage in a range of approximately 300 Vp-3,000 Vp, for example. Thus, such aberrant path of current flow has the potential to create an unintended patient burn injury to patient tissue at a sheath breach location.

SUMMARY

In one aspect a system detects a breach of an insulative sheath in a bipolar electrosurgical instrument. The system includes a first pulse detection circuit to detect a first HF signal component of the HF signal conducted on the lead and includes a second pulse detection circuit to detect a second HF signal component of the HF signal conducted on the shield. Phase difference sampling logic produce sample values indicative of a phase difference between the first HF signal component and the second HF signal component. Current detection logic detects current flow between the shield and anatomical tissue based upon the sample values.

In another aspect, a method is provided to detect a breach of an insulative sheath in a bipolar electrosurgical instrument. The method includes detecting pulses of a first HF signal component of the HF signal conducted on the lead and detecting pulses of a second HF signal component of the HF signal conducted on the shield. Sample values are produced that are indicative of a phase difference between the pulses of the first HF signal component and the second HF signal component. Current flow between the shield and anatomical tissue is detected based upon the sample values.

In yet another aspect a system detects a breach of an insulative sheath in a bipolar electrosurgical instrument. The system includes a first pulse detection circuit to detect a first HF signal component of the HF signal conducted on the lead and includes a second pulse detection circuit to detect a second HF signal component of the HF signal conducted on the shield. Magnitude difference sampling logic produce sample values indicative of a magnitude difference between the first HF signal component and the second HF signal component. Current detection logic detects current flow between the shield and anatomical tissue based upon the sample values.

In another aspect, a method is provided to detect a breach of an insulative sheath in a bipolar electrosurgical instrument. The method includes detecting pulses of a first HF signal component of the HF signal conducted on the lead and detecting pulses of a second HF signal component of the HF signal conducted on the shield. Sample values are produced that are indicative of a magnitude difference between the pulses of the first HF signal component and the second HF signal component. Current flow between the shield and anatomical tissue is detected based upon the sample values.

The scope of the invention is defined by the claims, which are incorporated into this section by reference. A more complete understanding of examples of the present invention will be afforded to those skilled in the art, as well as a realization of additional advantages thereof, by a consideration of the following detailed description of one or more examples. Reference will be made to the appended sheets of drawings that will first be described briefly.

BRIEF DESCRIPTION OF DRAWINGS

Examples of the present invention and their advantages are best understood by referring to the detailed description together with the drawings. It should be appreciated that like reference numerals are used to identify like elements illustrated in one or more of the figures. It should also be appreciated that the figures may not be necessarily drawn to scale.

DETAILED DESCRIPTION

Electrosurgical Instruments

Figure 1:
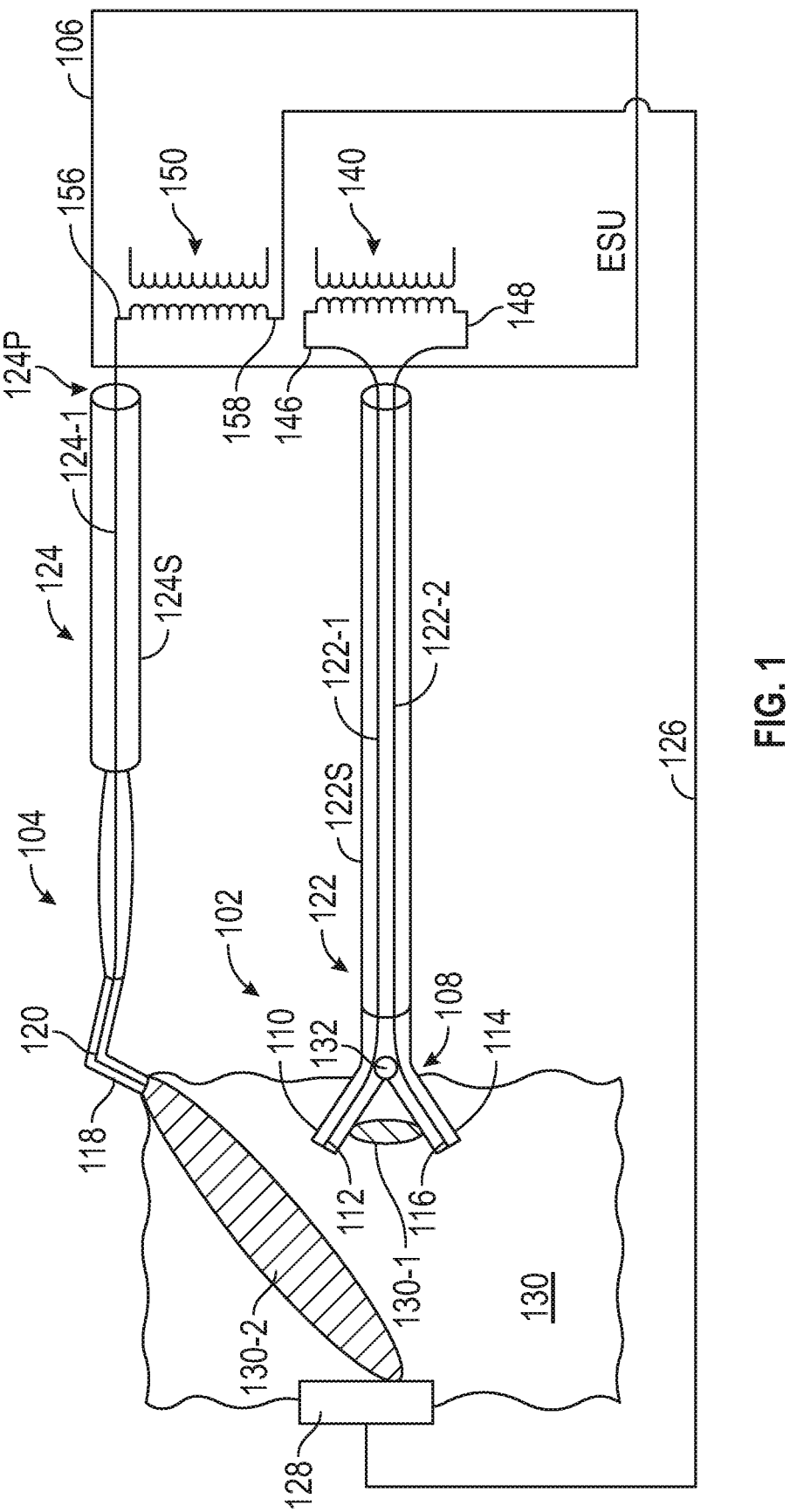
FIG. 1 is an illustrative schematic diagram showing an example bipolar surgical electrosurgical instrument and an example monopolar surgical electrosurgical instrument selectively coupled to receive electrosurgical signals from an electrosurgical generator unit.

FIG. 1 is an illustrative schematic diagram showing an example bipolar surgical electrosurgical instrument 102 and an example monopolar surgical electrosurgical instrument 104 selectively coupled to receive electrosurgical signals from an electrosurgical generator unit (ESU) 106. An electrosurgical signal typically is a high frequency signal (HF), ordinarily in a radio frequency range (RF) that has a voltage level suitable to achieve a desired surgical effect such as desiccation, coagulation, or vaporization of patient tissue 130, for example. The voltage level of an electrosurgical signal is selected according to the desired surgical effect. The first electrosurgical instrument (ESI) 102 includes a first end effector 108 that includes a first jaw member 110 including a first electrode 112 and a second jaw member 114 that includes a second electrode 116. The second ESI 104 includes a second end effector 118 that includes a single electrode, a monopolar electrode 120. A bipolar leads cable 122 includes first and second bipolar leads that extend between the ESU and the bipolar end effector 108. A first bipolar lead within the cable 122 is electrically coupled to the first electrode 112 within the first arm 110 of the bipolar end effector 108. A second bipolar lead within the cable 122 is electrically coupled to the second electrode 116 within the second arm 114 of the bipolar end effector 108. A monopolar lead cable 124 extends between the ESU 106 to the monopolar instrument 104. Monopolar current passes down monopolar electrical lead 124-1 to monopolar electrode 120 then through patient tissue 130-2 to a return conductor pad 128 that is placed in contact with patient tissue 130 which provides a return path for monopolar current through 126 back to ESU 106. Commonly assigned U.S. Provisional Patent Application, Ser. No. 62/513,287, filed May 31, 2017, entitled Electrosurgical Output Stage with Integrated DC Regulator, describes an ESU 106 in accordance with some embodiments, and is expressly incorporated herein in its entirety by this reference.

The end effector 108 of the bipolar ESI 102 includes an articulated jaw that includes first and second jaw members 110, 114 that articulate relative to one another about a pivot axis 132. At least one of the first and second jaw members 110, 114 is mounted to rotatably pivot about the pivot axis 132 between an open position in which the first and second jaws 110, 114 are spaced apart from each other and a closed position for grasping biological tissue 130-1 between them. The first and second electrodes 112, 116 are mounted upon the jaw members 110, 114 to electrically contact biological tissue 130-1 grasped between the first and second jaw members 110, 114. During normal operation, while the jaw members 110, 114 grip tissue 130-1 between them, the ESU 106 imparts a high frequency electrosurgical signal between the first and second electrodes 112, 116 to cause electrical current to flow through the tissue portion 130-1 grasped between the jaw members 110, 114 to impart heat to the first tissue portion 130-1 to thereby impart an electrosurgical surgical effect such as desiccation, coagulation, or vaporization, for example.

The end effector 118 of the monopolar ESI 104 includes the single third electrode 120 that may be placed in contact with a patient's biological tissue 130-2. During normal operation, the ESU 106 imparts a high frequency electrosurgical signal between the third electrode 120 and the return conductor pad 128 to cause electrical current to flow through a second tissue portion 130-2 disposed between the third electrode 120 and the return conductor pad 128 to cause electrical current to flow through the second tissue portion 130-2 to impart to the second tissue portion 130-2 an electrosurgical effect. The return conductor pad 128 has a surface area that is large enough so that patient tissue in physical contact with the pad has a large enough surface area so that return current to the ESU 106 spreads across a wide enough patient tissue area 130 to limit the current density sufficiently to avoid tissue burns or other trauma due to the return current, for example.

The bipolar ESI 102 ordinarily uses lower voltage, and therefore lower energy, than the monopolar second ESI 104. Because of the lower energy level, bipolar ESI 102 may have a more limited ability to cut and coagulate large bleeding areas and is more ideally used for those procedures where the first biological tissue portion 102 can be easily grabbed on both sides by the jaw members 110, 114 containing the first and second electrodes 112, 116. Thus, in bipolar surgery, the electrosurgical current in the patient is restricted to just the tissue between the jaw electrodes 112, 116, which may provide better control over the area being targeted and help prevent damage to other sensitive tissues.

The bipolar leads cable 122 and the monopolar leads cable 124 span a distance between the ESU 106 and the respective bipolar and monopolar ESIs 102, 104. The bipolar leads cable 122 includes an outer insulative sheath 122S, which may include insulating material that encloses first and second conductive bipolar leads 122-1, 122-2, often referred to as 'electrodes', that extend within it. The monopolar lead cable 124 includes a cable outer sheath 124S, which may include insulating material that encloses a third conductive monopolar lead 124-1 that extends within it.

The ESU 106 includes a first transformer circuit 140 to selectably couple an electrosurgical signal between the first and second bipolar leads 122-1, 122-2, also referred to as active and return leads. The ESU 106 controllably electrically couples and decouples respective first and second terminals 146, 148 of the first transformer 140 to and from the respective first and second bipolar leads 122-1, 122-2. The ESU 106 includes a second transformer circuit 150 to selectably couple an electrosurgical signal between the monopolar lead 124-1 and the third (return) conductor cable 126. More specifically, the ESU 106 is configured to controllably electrically couple and decouple the first and second terminals 156, 158 of the second transformer 150, respectively, to and from the third monopolar lead 124-1 at the proximal end portion 124P of the second cable 124 and the third (return) conductor cable 126.

Parasitic Capacitance within Bipolar Leads

Figure 2A:
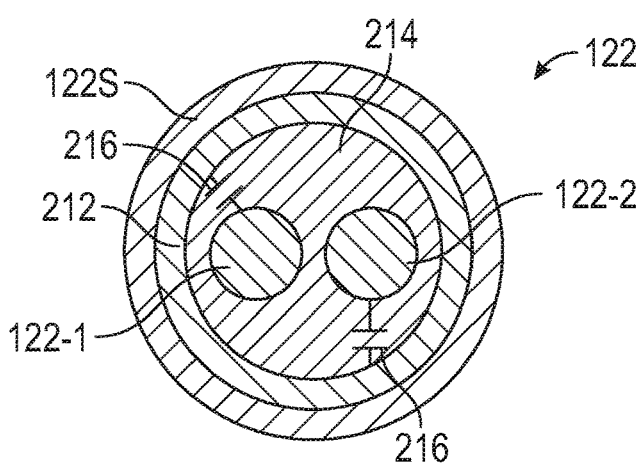
FIG. 2A is an illustrative axial cross-sectional view of the bipolar leads cable.
Figure 2B:
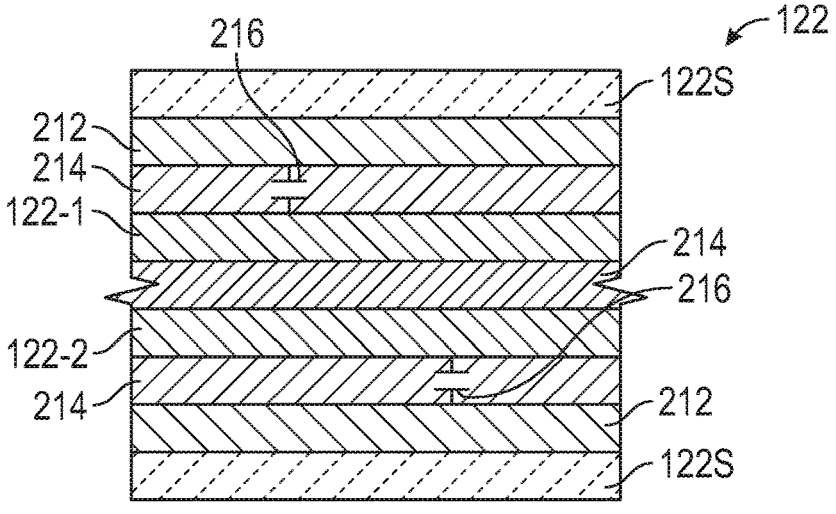
FIG. 2B is an illustrative longitudinal cross-sectional view of the bipolar leads cable with an intact outer sheath.
Figure 2C:
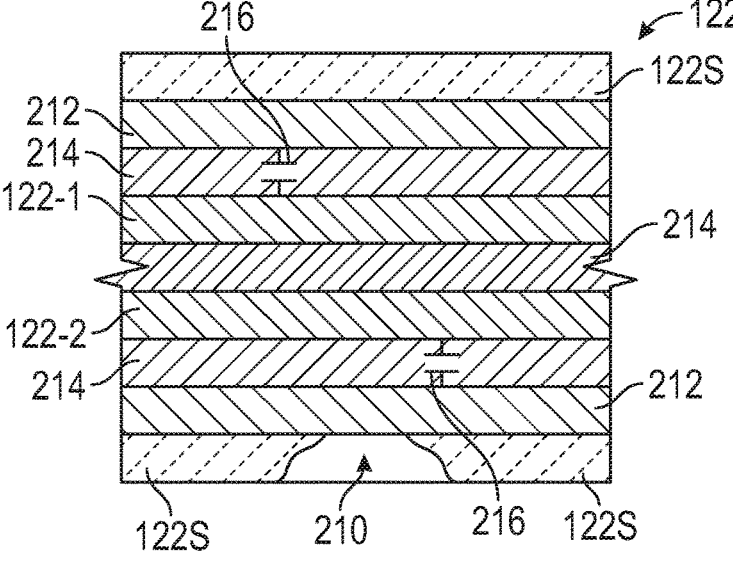
FIG. 2C is an illustrative longitudinal cross-sectional view of the bipolar leads cable with a breached outer sheath.

FIG. 2A is an illustrative axial cross-sectional view of the bipolar leads cable 122. FIG. 2B is an illustrative longitudinal cross-sectional view of the bipolar leads cable 122 with an intact outer sheath 124S. FIG. 2C is an illustrative longitudinal cross-sectional view of the bipolar leads cable 122 with a breached 210 outer sheath 122S. The bipolar leads cable 122 includes an elongated tubular shield conductor 212 that is surrounded by the non-conducting tubular outer insulating sheath 122S. The shield 212 surrounds the first and second (active and return) bipolar leads 122-1, 122-2 to provide protection against unintended parasitic capacitive coupling of monopolar electrosurgical energy from the bipolar leads 122-1, 122-2 to the patient. Capacitively coupled energy can potentially lead to electrical arcing or conduction to patient tissue 130 that may cause thermal injury to the patient. Parasitic capacitance 216 between the shield 212 and the bipolar leads 122-1, 122-2, allows the unintended transfer of monopolar energy from ESI 104 to the bipolar leads 122-1, 122-2 and the shield 212. The insulating sheath 122S electrically isolates the capacitively coupled conductor shield 212 from the patient tissue 130. A dielectric material 214 is disposed between the shield 212 and the first and second bipolar leads 122-1, 122-2 and between the first and second bipolar leads themselves. A breach 210 in the insulation sheath 122S such as that shown in FIG. 2C, can occur due to unintended or aggressive use during the surgical procedure, such as another instrument (not shown) physically contacting the bipolar leads cable 122 during a surgical procedure, for example.

Aberrant Current Flow to Due to Breach in Insulative Sheath

Figure 3A:
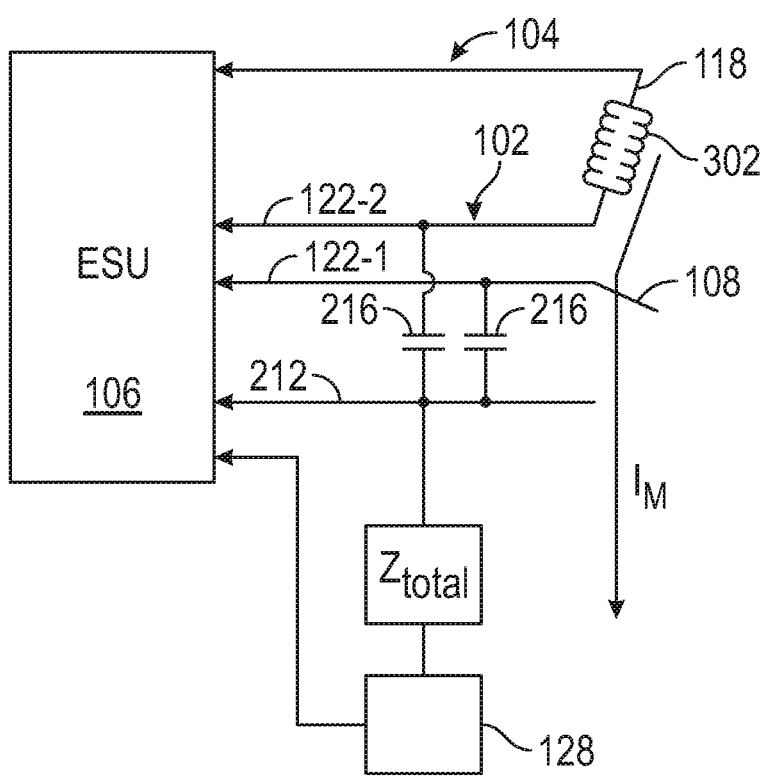
FIG. 3A is an illustrative physical model representing an electrical contact point between an activated monopolar end effector and the bipolar end effector.

FIG. 3A is an illustrative physical model representing an electrical contact point 302 between an activated monopolar end effector 118 and the bipolar end effector 108. A high frequency (HF) monopolar current $I_M$ imparted to the bipolar instrument leads is parasitically coupled to the protective shield. An impedance $Z_{total}$, which includes patient tissue impedance electrically couples the shield to the return pad 128, which is electrically coupled to the ESU (not shown). Thus, aberrant monopolar current $I_M$ flows from the monopolar electrode 120 to bipolar jaw electrode 116 (or

112) to one or both of bipolar leads 122-1 and 122-2 to shield 212 to a path having impedance $Z_{total}$, to return lead (not shown). In general, monopolar signal components on the two bipolar leads have matching phases and magnitudes. As explained more fully below, if the sheath 122S is intact, $Z_{total}$ includes impedance of patient tissue ($R_P$) plus impedance of the insulative sheath resistance ($R_{sh}$). However, if the sheath 122S is breached, $Z_{total}$ includes only impedance of patient tissue ($R_P$).

Figure 3B:
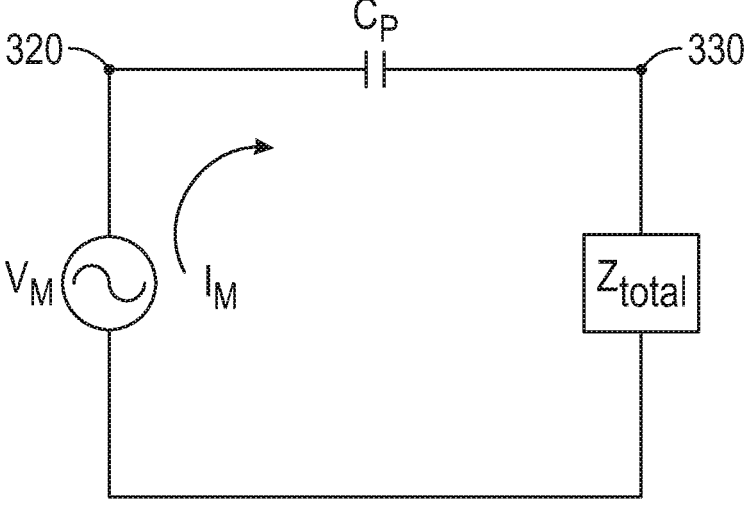
FIG. 3B is an illustrative circuit model representing the physical model of FIG. 3A.

FIG. 3B is a simplified illustrative circuit model representing the physical model of FIG. 3A. the circuit model includes a monopolar voltage source ($V_M$), a parasitic coupling capacitance $C_P$, and a path impedance $Z_{total}$, which includes patient tissue, between the shield and the return pad. A bipolar lead node 320 is coupled between $V_M$ and $C_P$. A bipolar shield node 330 is coupled between $C_P$ and $Z_{total}$. The monopolar current $I_M$ flows within the circuit model. When the insulative sheath is breached (i.e. no sheath resistance), $Z_{total}$ arises primarily due to patient resistance which is primarily resistive and typically measures in a range often to thousands of ohms. When the insulative sheath is intact $Z_{total}$ arises primarily due to sheath resistance which is which typically measures in a range of about 1 M ohm or greater.

$$Z_{equivalent} = Z_{total} - j * X_C$$

$Z_{equivalent}$ is the total impedance of the branch: the impedance arising from the combination of Xc and $Z_{total}$. When the sheath is intact $Z_{total}$ includes the sheath (Rsh) and patient (Rp) resistance in overall impedance of the branch. In this case the resistance of the branch is much larger than the reactance, since $Z_{total} >> Xc$ when sheath is intact. As such the branch is much more resistive than reactive and the current through the branch leads the voltage driving the current through the branch by a small amount. This leads to a small phase shift in voltage between 320 and 330. 320 is the bipolar electrode and 330 is the bipolar shield. These are the electrical points at which we measure phase shift.

When a sheath breach occurs, implying the shaft of the bipolar instrument comes into direct contact with the patient, the sheath resistance, Rsh, is not included in $Z_{total}$ of the model. When this happens, the resistance is on the same order of magnitude as the reactance and the overall impedance of the branch becomes more reactive than when an intact sheath is present. The current through the branch now leads the driving voltage by a larger amount than when an intact sheath is present. The leading shift in current through the branch creates a larger phase shift in voltages between 320 and 330. These are the electrical points at which we measure phase shift. We set a phase shift threshold to guarantee that if crossed we must have a sheath breach. It will be appreciated that $Z_{total}$ plays a role in phase shift between an $I_M$ current component at the bipolar lead node 320 and parasitically coupled $I_M$ current component at the shield node 330. When $Z_{total}$ is large (i.e. intact sheath), then $Z_{total} >> Z_C$ and a phase shift, $\theta_{zequ}$, between bipolar and sheath nodes 320, 330 is smaller. When $Z_{total}$ is small (i.e. breached sheath), the phase shift $\theta_{zequ}$ is larger and a phase shift between the nodes 320, 330 is larger.

Figure 4A:
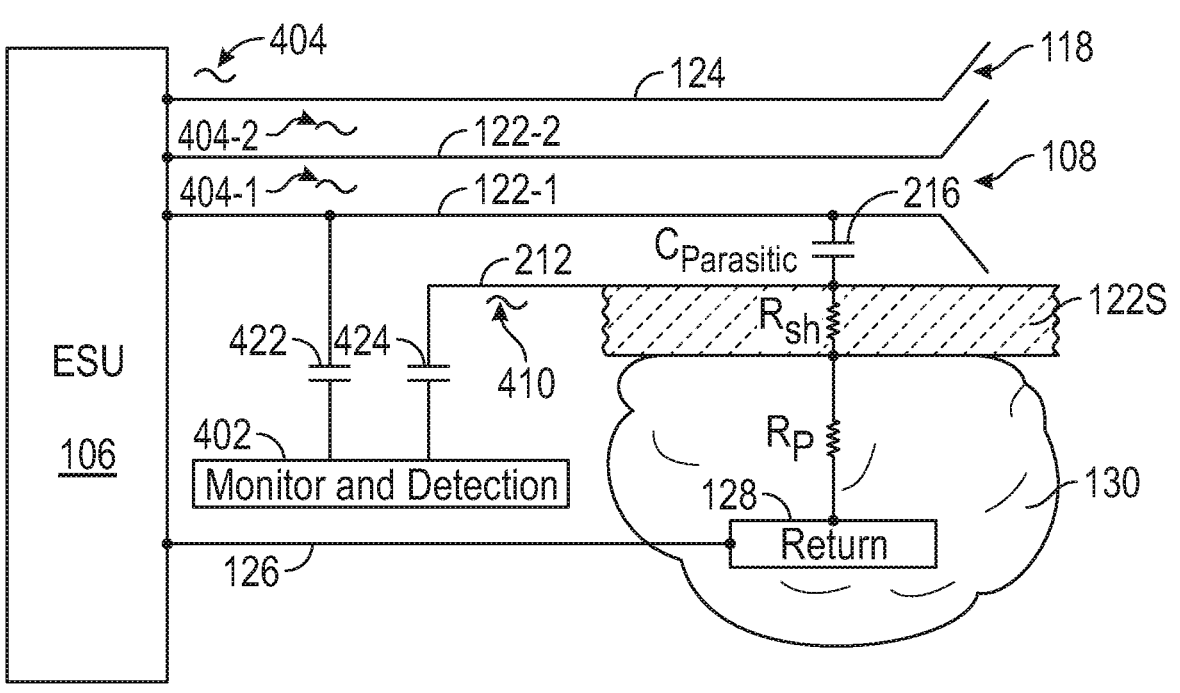
FIGS. 4A-4B are illustrative block diagrams representing an example monitor system coupled to a bipolar ESI to monitor characteristics of a high frequency (HF) signal component parasitically coupled to a shield conductor, during electrical contact between an activated monopolar end effector and a bipolar end effector when an insulative sheath is intact (FIG. 4A) and when the sheath is breached (FIG. 4B).
Figure 4B:
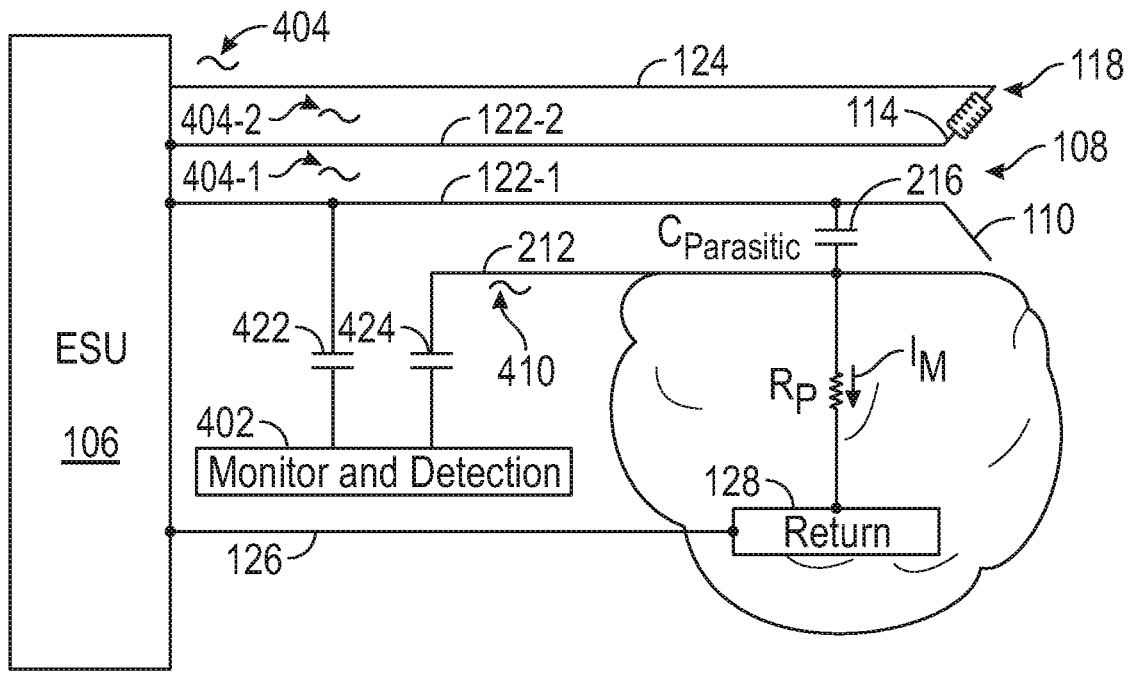

Monitor and Detection Circuit Coupled to Detect Change in Characteristic of HF Signal Coupled to Shield by Parasitic Coupling Capacitance FIGS. 4A-4B are illustrative block diagrams representing an example monitor and detection system 402 coupled to a bipolar lead 122-1 (or 122-2) to monitor characteristics of an HF signal parasitically coupled to a shield conductor 212 to detect electrical discharge current between an activated monopolar end effector 118 and a bipolar end effector 108. FIG. 4A shows electrical characteristics of a current path between the shield conductor 212 and the monopolar instrument return pad 128 when an insulative sheath 122S is intact. FIG. 4B shows electrical characteristics of a current path between the shield conductor 212 and the monopolar instrument return pad 128 when the insulative sheath 122S is breached. The current path is displaced from bipolar end effector 108. More particularly, the current path includes a portion of the shield 212 that ordinarily is electrically isolated from patient tissue 130 by the insulative sheath 122S. As explained below, the intact the insulating sheath 122S shown in FIG. 4A prevents the parasitic capacitive coupling of current from the conductive shield 212 to patient tissue 130. However, the breached insulating sheath 122S shown in FIG. 4B, permits parasitic capacitive coupling of current from the conductive shield 212 to patient tissue 130. The monitor and detection circuit 402 detects potentially dangerous discharge of electrical energy to patient tissue 130, during electrical contact between an activated monopolar end effector 118 and a bipolar end effector 108. More particularly, a first example monitor and detection circuit 402 described below with reference to FIG. 5, detects a change in current phase at the shield 212 caused by formation of a series impedance divider due to a breach in the sheath 122S in which the parasitic coupling capacitance 216 and the patient impedance $Z_P$ comprise two impedance elements of the series impedance divider, Moreover, a second example monitor and detection circuit 402 described below with reference to FIG. 8, detects a change difference in voltage magnitude between the shield 212 and the bipolar electrical lead 122-1. When the sheath is intact Rsh is present and the voltage difference between 122-1 and 212 is small. When the sheath is breached and the shield comes into contact with the patient tissue, only Rp is present, and the voltage difference between 122-1 and 212 is larger than with an intact sheath. A threshold is set in the middle of these two differences. If difference in voltage is larger than a set threshold monopolar energy is disabled.

Referring to FIGS. 4A-4B, the parasitic coupling capacitance ($C_{parasitic}$) 216 typically is in a range of approximately 120 pF, which approximately 3800 ohms (Reactance). The insulative sheath resistance ($R_{sh}$) typically is in a range of about 1 M ohm to about 1 G ohm (Resistive). The patient resistance ($R_P$) is typically in a range of tens to thousands of ohms (Resistive). Referring to FIG. 4A, with an intact insulative sheath 122S very little current can be parasitically coupled to the patient tissue 130 due to the large sheath resistance ($R_{sh}$) coupled in series between the parasitic capacitance ($C_{parasitic}$) 216 and the patient resistance ($R_P$). Referring to FIG. 4B, however, with a breached insulative sheath, a larger current can be parasitically coupled to the patient tissue 130 due to the parasitic capacitance ($C_{parasitic}$) 216 being directly coupled in series to the patient resistance ($R_P$). Referring to both FIGS. 4A-4B, ESU 106 produces an HF monopolar signal 404 on a circuit that includes the monopolar lead 124 between the ESU 106 and the monopolar end effector 118 and includes a path within patient tissue 130 between the monopolar end effector 118 and the return conductor pad 128, and that follows a path on conductor line 126 between the return conductor pad 128 and the ESU 106. During normal operation, the monopolar signal 404 conducted within the monopolar instrument 104 is isolated from the bipolar instrument 102. However, when the activated monopolar end effector 118 electrically contacts the bipolar end effector 108, the monopolar HF signal 404 is coupled to bipolar line 122-1, indicated by a first monopolar signal component 404-1, and is coupled to bipolar line 122-2, indicated by another first monopolar signal component 404-2, Thus, the electrical contact between the activated monopolar instrument and the bipolar instrument results in flow of monopolar signal current on the bipolar leads.

Still referring to both FIGS. 4A-4B, a first coupling capacitor 422 couples to the monitor and detection circuit 402 a monopolar signal component 404-1 (or 404-2) coupled to the bipolar lead 122-1 (or 122-2). A second coupling capacitor 424 couples to the monitor circuit 402, a second high frequency (HF) monopolar shield signal component 410 coupled by the parasitic coupling capacitor 216 from one of the bipolar leads 122-1, 122-2 to the conductive shield 212. It will be appreciated that the coupled monopolar signal components 404-1, 404-2 have matching phases and magnitudes. It also will be appreciated that the second HF monopolar shield component signal 410 comprises a parasitically coupled portion of at least one of the monopolar signal components 404-1, 404-2 coupled to the bipolar leads 122-1, 122-2. The monitor and detection circuit 402 determines whether a characteristic of the second HF monopolar shield signal component 410 coupled by the parasitic coupling capacitor 216 to the conductive shield 212 indicates aberrant current $I_M$ due to a breach of the protective sheath 210. Aberrant current flow at a breach location causes a change in a characteristic of the portion of the HF shield signal component 410 coupled from one or both of the bipolar leads 122-1, 122-2 to the conductive shield 212 by the parasitic coupling capacitor 216.

Figure 5:
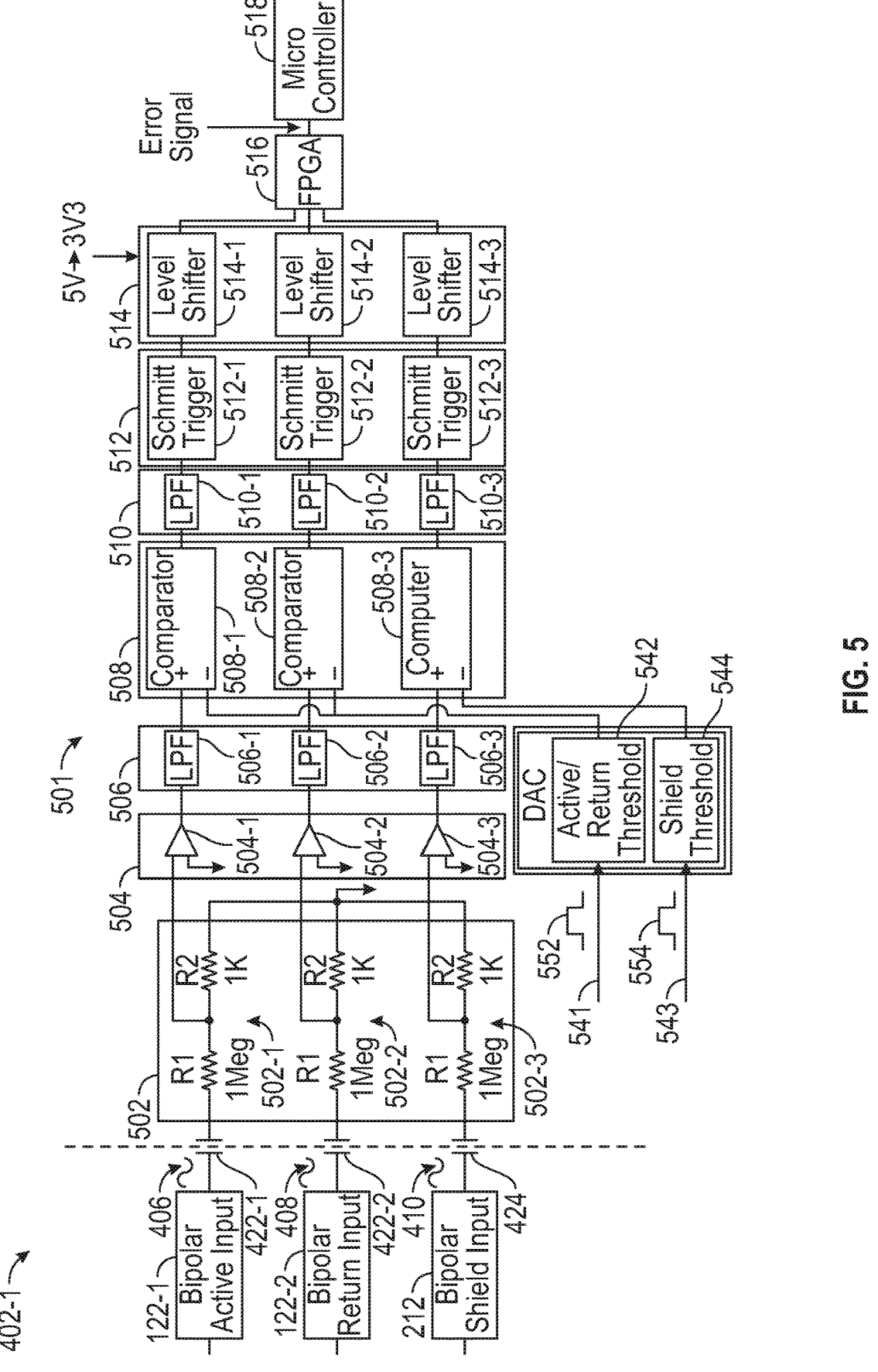
FIG. 5 is an illustrative schematic diagram showing details of a first example monitor circuit that detects RF signal phase shift change events.

Monitor and Detection Circuit Configured to Detect Change in Phase Shift Characteristic of HF Signal Coupled to Shield by Parasitic Coupling Capacitance FIG. 5 is an illustrative schematic diagram showing details of a first example monitor and detection circuit 402 that detects RF signal phase shift change events. The inventors realized that the patient tissue in which the aberrant monopolar current $I_M$ flows has an impedance that influences characteristics of an RF signal coupled to the shield 212 by the parasitic coupling capacitance 216 between the first and second bipolar leads 122-1, 122-2 and the shield 212. In particular, a phase shift arises from an impedance divider formed by the parasitic coupling capacitance 216 and an impedance $Z_P$ that includes patient tissue impedance, and that also includes an insulative sheath impedance if the sheath is intact and not breached.

Coupling capacitors 422-1, 422-2 couple the first HF monopolar signal components 404-1, 404-2 to the first example monitor and detection circuit 402. Coupling capacitor 424 couples the second HF monopolar shield signal component 410 to the first example monitor circuit 402. The coupling capacitors 422-1, 422-2, and 424 each includes a high impedance PCB embedded parallel plate capacitor.

The first example circuit 402 includes pre-processing circuitry 501 that includes an input voltage divider circuit block 502, an input amplifier circuit block 504, a first low pass filter block 506, a comparator circuit block 508, a second low pass filter (LPF) block 510, a Schmidt trigger circuit block 512, and a voltage level shifting circuit block 514. Output of the pre-processing circuitry 501 is provided to a first example logic circuit block 516, which determines a change in a phase shift characteristic of the second HF monopolar signal component 410 coupled to the conductive shield 212 in relation to the first HF monopolar signal component(s) 404-1, 404-2 coupled to the bipolar lead(s) 122-1, 122-2. In the first example logic circuit 516 includes a field programmable gate array (FPGA). A processor circuit 518 produces control signals based upon the phase shift characteristic determined by the monitor and detection circuit 402.

In the first example monitor and detection circuit 402, the detected characteristic is a phase relationship between HF monopolar signal components 404-1, 404-2 on one of the bipolar leads 122-1, 122-2 and the HF monopolar signal component 410 coupled to the conductive shield 212. During activation of a monopolar ESI 104, if the monopolar electrode 118 comes into contact with either bipolar jaws 110, 114, the first example monitor and detection circuit 402 measures a phase difference between the HF monolithic signal components 404-1, 404-2 on the bipolar lead(s) 122-1, 122-2 and the HF monopolar signal component 410 capacitively coupled to the bipolar shield 212. If there is no breach in the sheath, then there is negligible phase difference between the signal components. However, if a breach 210 occurs in the protective sheath 122S and the protective shield 212 comes into contact with patient tissue 130, an aberrant monolithic current $I_M$ flow across the parasitic coupling capacitance 216 causes a considerable phase shift between an HF monopolar signals present on the bipolar leads 122-1, 122-2 and an HF monopolar signal present on the shield 212. The first example monitor and detection circuit 402 measures this phase shift difference. Size and duration of the phase shift is used to determine breach occurrence. For example, a phase shift difference greater than a specified threshold indicates a tear in the insulative sheath. In the first example monitor and detection circuit, 402 the processor 518 generates control signals based upon the determined size and duration of a measured phase shift. The control signals cause one or more of terminating monopolar energy delivery to prevent patient delivery, sending a message to a user (e.g., a surgeon) or saving data to a storage device for later analysis, for example.

The first example monitor and detection circuit 402 includes an input signal pulse detection channel for each received HF monopolar signal component. A first pulse detection circuit channel pre-processes the HF monopolar signal component 404-1 on the bipolar lead 122-1 for input to the first example logic circuit 516. A second pulse detection circuit channel pre-processes the HF monopolar signal component 404-2 on the bipolar return lead 122-2 for input to the first example logic circuit 516. A third pulse detection circuit channel pre-processes the HF monopolar signal component 410 coupled to the conductive shield 212 for input to the first example logic circuit 516.

Referring to the first pulse detection circuit channel, a first coupling capacitor 422-1 couples the HF monopolar signal component 404-1 from the active bipolar lead 122-1 to the input voltage divider block 502, where a first divider circuit 502-1, which includes resistors $R_1$, $R_2$ coupled as shown, divides a voltage level of the HF monopolar signal component 404-1 received on the first channel to a voltage level suitable for input to the voltage amplification block 504, which includes a first amplifier circuit 504-1 to amplify the voltage level of the received first channel RF signal. A first low pass filter 506-1 within the first low pass filter block 506 low pass filters the amplified first channel HF signal. A first comparator circuit 502-1 within the comparator block 508 compares the low pass filtered first channel HF signal with a bipolar lead, threshold detection signal to convert the first channel HF signal to a square wave signal. A first digital-to-analog converter (DAC) circuit 542 converts a provided first digital signal value 552 on line 541 to generate a first (bipolar lead) threshold detection signal. A typical received first channel RF signal has a sinusoidal waveform, and each pulse consists of one-half of a sinusoidal signal cycle. The first comparator circuit 508-1 converts the received first channel RF signal waveform to a square waveform based upon comparison of rising and falling edges of the sinusoidal signal with the shield threshold detection signal. A first low pass filter 510-1 within the second LPF block 510 low pass filters the first channel signal, which has been converted to a square wave waveform. It will be appreciated that the first LPFs 506 filter the raw incoming signal and the second LPFs 510 filter noise of the digital signal output from the comparators 508. A first Schmidt trigger circuit 512-1 within the Schmidt trigger block 512 acts as a noise filter to remove noise from the filtered first channel square wave signal. A first level shifting circuit 514-2 within the level shifting block 514 shifts a voltage level of the smoothed first channel HF square wave signal to a voltage level suitable for input to the first example logic circuit 516. Thus, it will be appreciated that the comparator and the Schmidt trigger cooperate to convert the first HF monopolar signal component 404-1 to a substantially noise-free square wave signal.

The second and third pulse detection circuit channels of the first example monitor and detection circuit 402 pre-process the respective HF monopolar signal component 404-2 on the bipolar lead 122-2 and the HF monopolar signal component 410 on the shield 212 for input to the first example logic circuit 516. The pre-processing of the HF monopolar signal components 404-2, 410 is similar to the pre-processing of the HF monopolar signal component 404-1 except that a third comparator 508-3 compares the HF monopolar shield component signal 410 with second active/return threshold signal produced by a second DAC 544, which converts a provided second digital signal value 554 on line 543 to generate a second (shield) threshold detection signal. Operation of circuit components in the second and third channels and pre-processing of the second and third channel RF signals on the second and third channels will be readily understood by persons of ordinary skill in the art by references to the drawings and the above description of first channel pre-processing. Therefore, in the interest of conciseness, second and third channel pre-processing will not be described in detail herein.

Figure 6:
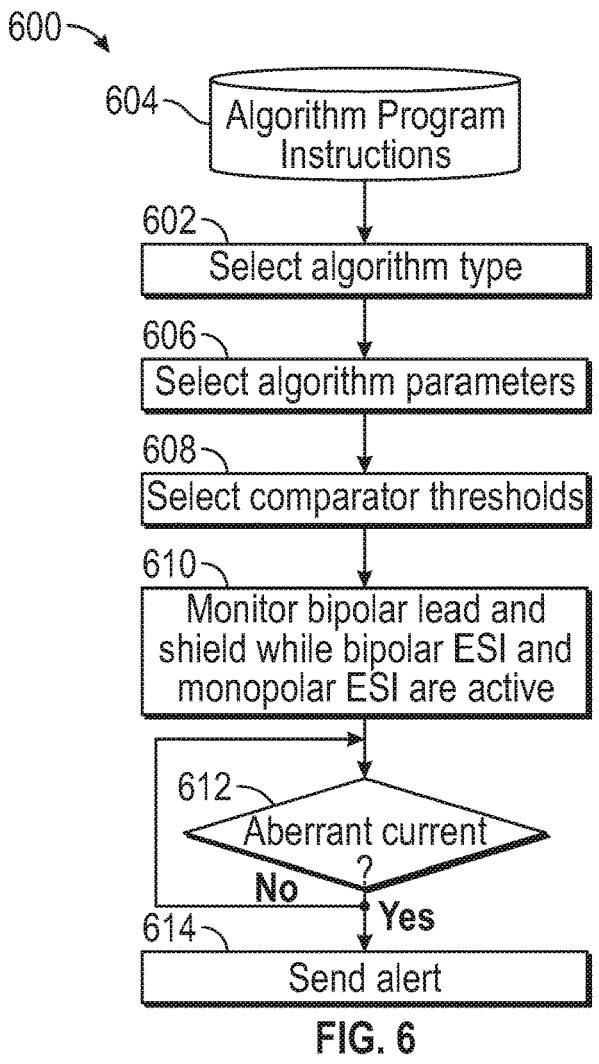
FIG. 6 is an illustrative flow diagram representing a monitoring process to monitor a phase relationship between first HF monopolar signal component and a second HF monopolar signal component to detect an occurrence of electrical current flow within patient tissue indicative of a breached insulative sheath.

FIG. 6 is an illustrative flow diagram representing a monitoring process 600 to monitor a phase relationship between HF monopolar signal components 404-1, 404-2 and an HF monopolar shield signal component 410 to detect an occurrence of aberrant monopolar current flow $I_M$ within patient tissue 130 indicative of a breached insulative sheath 122S. The first example logic circuit 516 is configured to perform the first monitoring process of FIG. 6. A user provides an input command to the first input logic module 602 to select an algorithm from a storage memory device 604 to configure the logic circuit 516. A storage memory device 604 stores multiple different selectable program instruction to configure the logic device 516 to implement multiple different selectable algorithms, described below, to detect an occurrence of aberrant current flow. A user provides an input command to a second input logic module 606 to input parameters for the selected algorithm. Example input parameters include length of sampling window and phase threshold. A user provides input commands to a third input logic module 608 to configure the logic circuit 516 to select comparator thresholds. More particularly, the user provides an input command to cause provision of the first digital signal 552 to the first DAC 542 to set the shield signal threshold detection level for the first and second comparator 508-1, 508-2. The user provides an input command to cause provision of the second logic signal 554 to second DAC 544 to set the threshold detection signal for the third comparator 508-3. The comparator threshold signals are set to cause the comparators to generate digital outputs in response to sinusoidal input signals crossing selected thresholds. Different comparator threshold settings can be used for the HF monopolar signal components 404-1, 404-2 on the one hand and for the HF monopolar shield signal component 410 on the other because there can be a difference in voltage amplitude introduced due to the parasitic coupling capacitance. A fourth phase difference sampling logic module 610 monitors a phase relationship between an HF signal 404-1, 404-2 coupled from a bipolar lead 122-1, 122-2 and an HF monopolar signal component 410 coupled from the shield 212. A fifth phase shift aberrant current detection logic 612 configures the first example logic circuit 516 to evaluate the phase relationship between the coupled monopolar signal component 404-1, 404-2 and the coupled HF shield signal component 410 based upon the selected algorithm and the selected comparator thresholds to determine whether there has been an occurrence of an aberrant monopolar current $I_M$ within patient anatomy 130 due to contact between the two ESIs in concert with a breach in the insulative sheath. A control loop including the fourth and fifth logic modules 610, 612 continues to run while the bipolar and monopolar instruments 102, 104 are active unless the fifth module detects 612 an aberrant current. A sixth alerts logic module 614 configures the first example logic circuit 516 to send a control signal to the processor 518 in response to a detection of an aberrant current flow. As explained above, in response to receiving a signal indicating an occurrence of an aberrant current, the processor 518 provides one or more control signals to alert the processor 518 to cause one or more of terminating monopolar energy delivery to prevent patient delivery, sending a message to a user (e.g., a surgeon) or saving data to a storage device for later analysis, for example.

Figure 7:
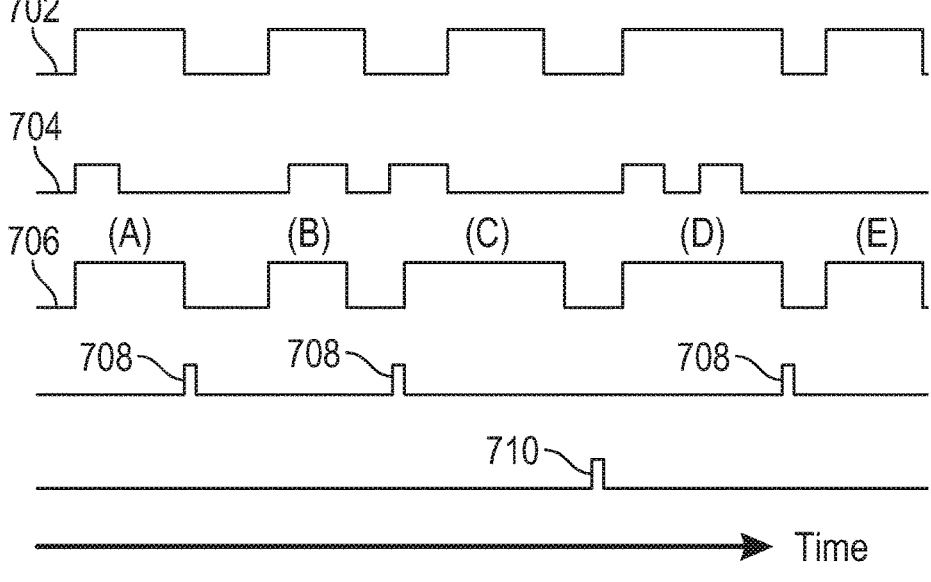
FIG. 7 is an illustrative signal diagram showing example signals produced by the first example monitor circuit during the process of FIG. 6.

FIG. 7 is an illustrative signal diagram showing example signals produced by the first example monitor circuit during the process of FIG. 6. RF bipolar square wave signals and the HF shield square wave signals produced by the first, second, and third pulse detection circuit channels are received as input at the logic circuit 516. The HF bipolar square wave signal 702 shown in FIG. 7 represents a pre-processed version of one of the HF monopolar signal components 404-1, 404-2 coupled from a bipolar lead 122-1, 122-2 that has been conditioned by one of the first and second pulse detection circuit channels of the pre-processing circuitry 501. The HF shield square wave signal 704 represents a version of an HF monopolar shield signal component 410 coupled from the shield 212 that has been conditioned by the third pulse detection circuit channel of the pre-processing circuitry 501. A pulse sampling window signal 706 is produced by internal logic of logic circuit 516 and represents a sequence of sampling time intervals in which the logic circuit 516 determines a sequence of phase relationships between pulses of the HF square wave signal 702 and pulses of the HF shield square wave signal 704. During successive sampling windows, the logic circuit 516 produces a good phase event sample pulse signal 708 in response to a determination that the HF bipolar lead and HF shield square wave signals have substantially matching phases, and the logic circuit 516 produces a bad phase event sample pulse signal 710 in response to a determination that the RF bipolar and RF shield square wave signals have non-matching phases. Referring to FIGS. 6-7, the fourth phase difference sampling logic module 610 represented in FIG. 6 configures the logic circuit 516 to identify the occurrence times of centers of successive pulses of the HF bipolar square wave 702 by identifying the times of occurrence of their respective rising and falling edges. Similarly, the fourth phase difference sampling logic module 610 configures the logic circuit 516 to identify the occurrence times of centers of successive pulses of the HF shield square wave 704 by identifying the times of occurrence of their respective rising and falling edges. The fourth phase difference sampling logic module 610 configures the logic circuit 516 to evaluate the phase relationship of HF monopolar signal components 404-1, 404-2 on bipolar leads 122-1, 122-2 and HF monopolar shield signal components on the shield 212 during the successive sampling time windows based upon a measure of difference in occurrence times of square wave pulses corresponding to monopolar signal components on bipolar leads 122-1, 122-2 and square wave pulses corresponding to monopolar signal components on the shield 212 during the successive sampling time windows. For example, during each time window, the logic circuit 516 determines a difference in time of occurrence of a center of a pulse corresponding to a monopolar signal component 404-1, 404-2 on a bipolar lead 122-1, 122-2 and time of occurrence of a center of a pulse corresponding to a monopolar shield signal component 410 on the shield 212 during the time window. The fourth phase difference sampling logic module 610 configures the logic circuit 516 to produce a good phase event signal pulse 708, indicating no occurrence of an aberrant current event, for each sampling time interval in which the time difference between pulse centers is less than a threshold time difference. The fourth phase difference sampling logic module 610 configures the logic circuit 516 to produce a bad phase event signal pulse 710, indicating a possible occurrence of an aberrant current event, for each sampling time interval in which the time difference between centers of the pulses is greater than or equal to a threshold time difference. It is noted that the center points of the pulses are used for the phase shift determination since the widths of the square wave pulses is dependent upon the amplitude of the sine wave input, which varies with signal amplitude.

More particularly, for example, the illustrative signal diagram of FIG. 7 includes five sampling windows: (A)-(E). An example fourth phase difference sampling logic module 610 configures the logic circuit 516 to open a pulse sampling time window upon an occurrence of a leading edge of either of the HF bipolar square wave pulse 702 the HF shield square wave pulse 704. During the first example sampling window (A), a HF bipolar square wave pulse 702 and a HF shield square wave pulse 704 both occur within the threshold time difference, and therefore, a good phase event signal pulse 708 is produced. Similarly, during the second example sampling window (B), a HF bipolar square wave pulse 702 and a HF shield square wave pulse 704 both occur within the threshold time difference, and therefore, a good phase event signal pulse 708 is produced. In the illustrative example signal diagram, the second sampling window (B) closes early, after falling edge occurrences of both the pulse 702 and the pulse 704. As shown in the third example sampling window (C), if a sampling window opens while either a pulse 702 or a pulse 704 is received (e.g., is high), then the time at which the sampling window opens is considered to be the leading edge for that pulse. During the third example sampling window (C), the pulse 702 the pulse 704 are spaced in time by an amount greater than the threshold time difference, and therefore, a bad phase event signal pulse 710 is produced. An example fourth phase difference sampling logic module 610 is configured to handle a situation in which, for example, multiple pulses 702 or multiple pulses 704 occur during a sampling window, as shown in the fourth example sampling window (D). An example sampling logic module 610 can be configured to make a good/bad determination based upon the first pulse, the last pulse or the largest pulse or based upon the midpoint of the first rising edge and the last falling edge, for example. A determination is made for the fourth example sampling window (D) that the pulse 702 and the pulse 704 both occur within the phase difference threshold, and therefore a good phase event sample pulse signal 708 is produced. An example sampling logic module 610 can be configured such that during a sampling window when only one of two pulses 702, 704 occurs, neither a good pulse nor a bad pulse is produced. For example, during the fifth example sampling window (E), there is an occurrence of the pulse 702, but there is no occurrence of the pulse 704, and therefore, no good/bad pulse is produced.

The fifth aberrant current detection logic 612 of FIG. 6 configures the logic circuit 516 to use a selected phase-difference based algorithm configured according to selected algorithm parameters to detect aberrant current based upon an evaluation of a HF phase difference between monopolar signal components on the bipolar leads and monopolar signal components on the shield as indicated by a succession of good and/or bad pulses.

Algorithms to Detect Aberrant Current Based Upon Comparison of Component of an HF Signal Conducted on a Lead with a Component of the HF Signal Conducted on a Shield A first example selectable phase-difference based algorithm configures the logic circuit 516 to detect an occurrence of aberrant current in response to a continuous sequence of bad phase event sample pulses for at least a prescribed time duration. Selectable parameters for the first example phase-difference based algorithm include a phase difference threshold and the prescribed time duration. An example time duration typically is in a range one-half to three-fourths of the ESU period.

A second example selectable phase-difference based algorithm configures the logic circuit 516 to detect an occurrence of aberrant current in response to at least a prescribed number of bad phase event sample pulses (pulse count) during a prescribed time duration. Selectable parameters for the second example phase-difference based algorithm include a typical phase difference threshold of 30-60 degrees phase shift, and the prescribed bad phase event pulse count and the prescribed time duration. An example time duration typically is in a range five hundred micro-seconds to two milliseconds.

A third example selectable phase-difference based algorithm configures the logic circuit 516 to detect an occurrence of aberrant current in response to at least a prescribed number (count) of consecutive bad phase event sample pulses. Selectable parameters for the third example phase-difference based algorithm include a phase difference threshold and the prescribed consecutive count of bad phase event sample pulses. An example number of consecutive bad phase event sample pulses typically is in a range three to seven.

A fourth example selectable phase-difference based algorithm configures the logic circuit 516 to detect an occurrence of aberrant current in response to at least a prescribed number (count) of consecutive bad phase event sample pulses within a prescribed time duration. Selectable parameters for the fourth example phase-difference based algorithm include a phase difference threshold and the prescribed number of bad phase event pulses and the prescribed time duration.

A fifth example selectable phase-difference based algorithm configures the logic circuit 516 to detect an occurrence of aberrant current in response to observation of a prescribed ratio of bad phase event sample pulses to good phase event sample pulses over a prescribed time duration. Selectable parameter for the fifth example phase-difference based algorithm include a phase difference threshold and the prescribed number ratio and the prescribed time duration.

The ESU 106 produces different modes of bipolar lead signals for different surgical procedures. For example, the ESU 106 produces cut mode signals to cut tissue. Cut mode signals typically are comprised of a continuous (non-pulsed) output. The ESU 106 produces coagulate mode signals to coagulate tissue. Coagulate mode signals typically are pulsed at a very low duty cycle.). The ESU 106 produces blend mode signals to blend tissue. Blend mode signals typically have a duty cycle between continuous and the low duty cycle used for Coagulate.

An algorithm type can be selected using the first input module 602 based upon the monopolar output settings and the ESU mode. For example, the algorithm type may be selected based upon power or effect setting and mode (which implies duty cycle). Similarly, parameters can be selected using the second input module 604 based upon the monopolar output settings and the ESU mode such as power or effect setting and mode (which implies duty cycle).) Comparator thresholds can be selected using the third input module based upon the monopolar output settings and ESU mode. For example, the comparator thresholds can be selected based upon expected amplitude of HF output signals.

Figure 8:
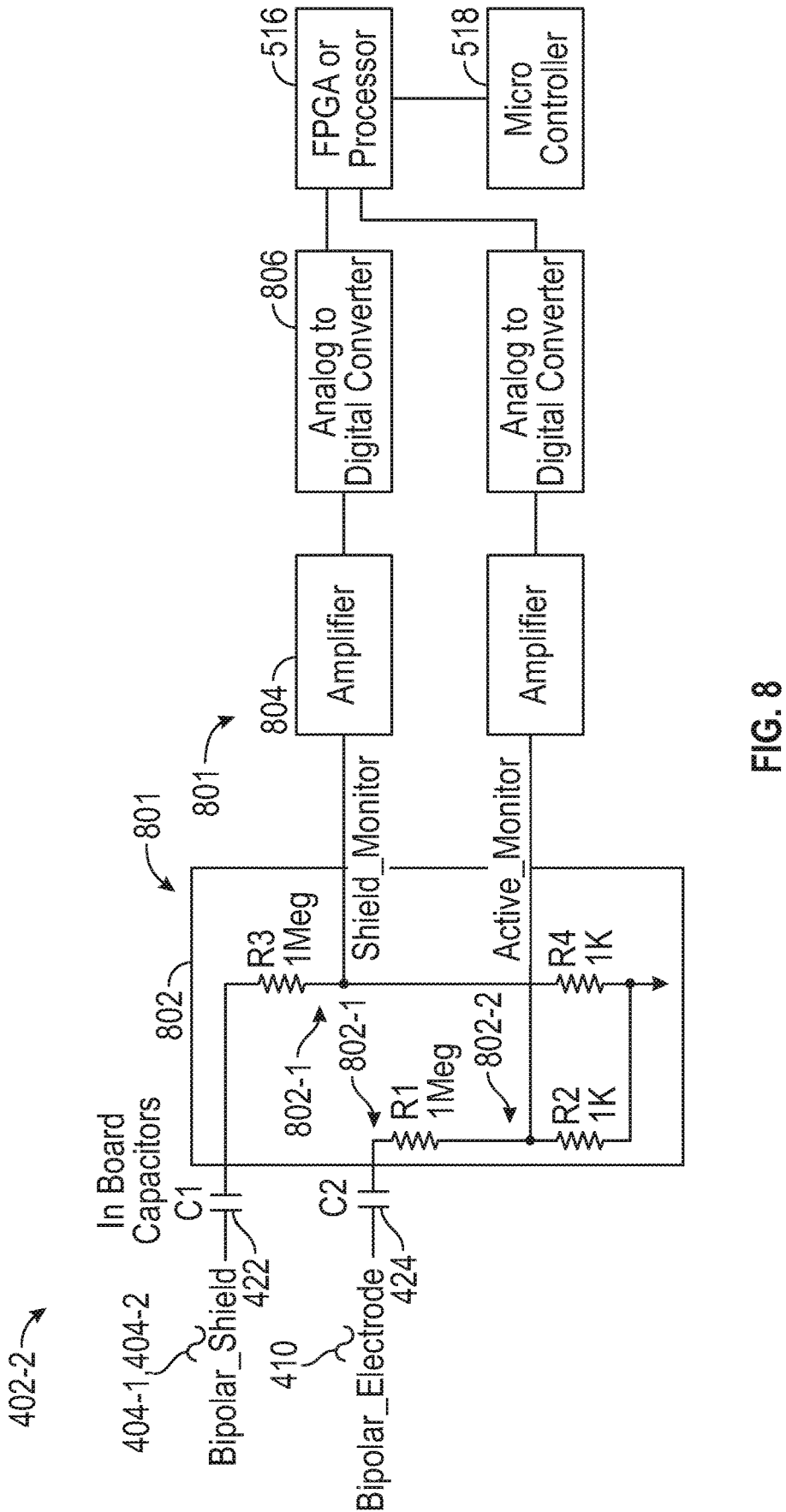
FIG. 8 is an illustrative schematic diagram showing details of a second example monitor and detection circuit that detects HF signal magnitude or phase change events.

Monitor and Detection Circuit Configured to Detect Change in Magnitude Characteristic of RF Signal Coupled to Shield by Parasitic Coupling Capacitance FIG. 8 is an illustrative schematic diagram showing details of a second example monitor and detection circuit 402-2 that detects RF signal magnitude change events. As explained above, the inventors realized that the patient tissue in which the aberrant monopolar current $I_M$ flows has an impedance $Z_P$ that influences characteristics of an HF monopolar signal component coupled to the shield by the parasitic coupling capacitance 216 between the first and second bipolar leads 122-1, 122-2 and the shield 212. In particular, magnitude of monopolar signal component on the shield changes with changes in the series impedance divider $Z_P$, which includes patient tissue resistance ($R_P$) in series with sheath resistance ($R_{sh}$), during aberrant monopolar current flow. Referring to equations, for example, as $Z_P$ approaches infinity, the monopolar shield voltage approaches the monopolar voltage on the bipolar leads. Thus, if the shield is intact, $Z_P$ is effectively infinite, no current flows through patient tissue 130 and a magnitude of the monopolar signal shield voltage matches a magnitude the monopolar signal bipolar lead voltage. However, if the shield is breached, $Z_P$ has a lower voltage magnitude, some monopolar signal component current flows through patient tissue 130, and a magnitude of the monopolar signal shield voltage is less than a magnitude of a voltage of the monopolar signal component on the bipolar leads. The second monitor and detection circuit 402-2 is configured to compare magnitude of at least one of the HF monopolar signal components 404-1, 404-2 with magnitude of HF monopolar shield signal component 410 to determine whether or not a potentially harmful monopolar current is flowing through patient tissue. If the magnitudes match, then a determination is made that there is no dangerous current flow. If the magnitudes differ by some prescribed magnitude, then a determination is made that there is a dangerous current flow. The second example monitor and detection circuit 402 includes pre-processing circuitry 801 that includes an input voltage divider circuit block 802, an input amplifier circuit block 804, and an analog to digital converter circuit block 806, which detects signal pulses. An output of the pre-processing circuitry 801 is provided to a logic circuit 516, which determines a change in a signal magnitude characteristic of the HF monopolar shield signal component 410 in relation to the HF monopolar signal components 404-1, 404-2. In the second example monitor circuit, the logic circuit 516 includes an FPGA. A processor circuit 518 produces control signals based upon the change in an RF shield signal magnitude characteristic determined by the second example monitor and detection circuit 402.

More specifically, the second example monitor circuit 402 includes first channel to pre-process one of the HF monopolar signal components 404-1, 404-2 and includes a second channel to pre-process the HF monopolar shield signal component 410. In most cases voltage magnitude is the same on both bipolar leads, and therefore, there is no need to measure voltage on both of them. Referring to the first channel, a first coupling capacitor 422 couples an HF monopolar signal component 404-1 (or 404-2) to the input voltage divider block, where a first divider circuit 802-1, which includes resistors $R_1$, $R_2$ coupled as shown, divide a voltage level of the HF monopolar signal component received on the first channel to a voltage level suitable for input to the voltage amplification block 804, which includes a first amplifier circuit (not shown) to amplify the voltage level of the received HF monopolar signal component. A first analog to digital converter (ADC) converts the amplified HF monopolar signal component and provides the amplified RF bipolar lead signal as input to the logic circuit 516.

The second channel of the preprocessing circuit 801 pre-processes the HF monopolar shield signal component 410. The pre-processing of HF monopolar shield signal component 410 coupled from the second coupling capacitor 424 is similar to the pre-processing of the HF monopolar signal component 404-1. Operation of circuit components in the second channel will be readily understood by persons of ordinary skill in the art by references to the drawings and the above description of first channel pre-processing. Therefore, in the interest of conciseness, second channel pre-processing will not be described in detail herein.

A monitoring process performed using the second example monitor and detection circuit 402-2 is similar to that described above with reference to FIG. 6 but without the select comparator block 608. Moreover, in the second monitor and detection circuit 402-2, the logic circuit 516 compares a voltage magnitude of a first monopolar signal component 404-1, 404-2 on at least one of the bipolar leads 122-1 or 122-2 with a voltage magnitude 410 of a second monopolar signal component on the shield 212 to detect potentially dangerous aberrant monopolar current flow. Furthermore, the logic circuit 516 of the second monitor and detection circuit 402-2 is configurable to perform the first through sixth example algorithms modified to compare signal component magnitude differences rather than signal component phase differences. More particularly, an example logic circuit 516 determines whether a magnitude of a difference between the voltage magnitude of a first monopolar signal component 404-1, 404-2 on at least one of the bipolar leads 122-1 or 122-2 with a voltage magnitude 410 of a second monopolar signal component on the shield 212 crosses a threshold magnitude difference. The logic circuit 516 of the example circuit 402-2 produces a good magnitude event sample pulse signal (not shown) in response to a determination that the HF bipolar lead and HF shield signals have substantially matching magnitudes; that is, the magnitude difference does not cross the magnitude difference threshold. The logic circuit 516 of the example circuit 402-2 produces a bad magnitude event sample pulse signal (not shown) in response to a determination that the HF bipolar lead and HF shield signals have non-matching magnitudes; that is the magnitude difference crosses the magnitude difference threshold.

The above description is presented to enable any person skilled in the art to create and use a system and method detect a breach in an insulative sheath of a bipolar electrosurgical instrument. Various modifications to the examples will be clear to those skilled in the art, and the generic principles defined herein may be applied to other examples and applications without departing from the scope of the invention. In the preceding description, numerous details are set forth for explanation. However, one of ordinary skill in the art will realize that the circuitry might be practiced without the use of these specific details. In other instances, well-known circuits and processes are shown in block diagram form in order not to obscure the description of the invention with unnecessary detail. Identical reference numerals may be used to represent different views of the same or similar item in different drawings and in the specification. Thus, the foregoing description and drawings of examples in accordance with the present invention are merely illustrative of the principles of the invention. Therefore, it will be understood that various modifications can be made to the examples by those skilled in the art without departing from the scope of the invention, which is defined in the appended claims.

What is claimed is:

1. A method to detect a breach of an outer insulative sheath in a bipolar electrosurgical instrument that includes, an end effector; a conductive lead to electrically couple the end effector to an electrosurgical generator unit; and an electrically conductive shield surrounding the conductive lead; wherein the outer insulating sheath surrounds the conductive shield, the method comprising:

detecting pulses of a first high frequency (HF) signal component of an HF signal conducted on the conductive lead;

detecting pulses of a second HF signal component of the HF signal conducted on the conductive shield;

producing a succession of sample values of the pulses of the first HF signal component and of the pulses of the second HF signal component;

determining, using the succession of sample values, phase differences between the pulses of the first HF signal component and the pulses of the second HF signal component;

detecting aberrant current flow between the conductive shield and anatomical tissue when the phase differences differ by at least a threshold phase amount.

2. The method of claim 1, wherein the detecting aberrant current flow between the conductive shield and anatomical tissue based upon the succession of sample values includes detecting aberrant current flow based upon a count of the sampled values with phase differences greater than the threshold phase amount.

3. The method of claim 1, wherein the detecting aberrant current flow between the conductive shield and anatomical tissue based upon the succession of sample values includes detecting aberrant current flow based upon a comparison of a count of the sampled values with phase differences greater than the threshold phase amount and a count of the sampled values with phase differences less than the threshold phase amount.

4. The method of claim 1, wherein the detecting aberrant current flow between the conductive shield and anatomical tissue based upon the succession of sample values includes detecting aberrant current flow in response to a continuous sequence of sampled values with phase differences greater than the threshold phase amount for a predetermined time duration.

5. The method of claim 1, wherein the detecting aberrant current flow between the conductive shield and anatomical tissue based upon the succession of sample values includes detecting aberrant current flow in response to detecting an occurrence of a predetermined number of sampled values with phase differences greater than the threshold phase amount during a predetermined time duration.

6. The method of claim 1, wherein the detecting aberrant current flow between the conductive shield and anatomical tissue based upon the succession of sample values includes detecting aberrant current flow in response to detecting an occurrence of a predetermined number of consecutive sampled values with phase differences greater than the threshold phase amount.

7. The method of claim 1, wherein the detecting aberrant current flow between the conductive shield and anatomical tissue based upon the succession of sample values includes detecting aberrant current flow in response to detecting an occurrence of a predetermined ratio of sampled values with phase differences greater than the threshold phase amount and sampled values with phase differences less than the threshold phase amount during a predetermined time duration.

8. The method of claim 1, wherein the producing the succession of sample values includes producing the succession of sampled values using a succession of sampling windows, and wherein the determining the phase differences includes determining phase differences between the center of the pulses of the first HF signal component and the center of the pulses of the second HF signal component during the sampling windows.

9. The method of claim 8, wherein the detecting aberrant current flow between the conductive shield and anatomical tissue based upon the succession of sample values includes detecting aberrant current flow in response to detecting an occurrence of a predetermined number of sampled values with phase differences greater than the threshold phase amount during a predetermined time duration.

10. The method of claim 1, wherein the succession of sample values are indicative of a magnitude difference over a time interval between the first HF signal component and of the second HF signal component; and wherein detecting includes detecting the aberrant current flow based upon the succession of sample values indicating that the first HF signal component and the second HF signal component have magnitudes that differ by at least a threshold magnitude amount.

11. The method of claim 10, wherein the detecting aberrant current flow between the conductive shield and anatomical tissue based upon the succession of sample values includes detecting aberrant current flow based upon a count of the sampled values with magnitude differences greater than the threshold magnitude amount.

12. The method of claim 10, wherein the detecting aberrant current flow between the conductive shield and anatomical tissue based upon the succession of sample values includes detecting aberrant current flow based upon a comparison of a count of the sampled values with magnitude differences greater than the threshold magnitude amount and a count of the sampled values with magnitude differences less than the threshold magnitude amount.

13. The method of claim 10, wherein the detecting aberrant current flow between the conductive shield and anatomical tissue based upon the succession of sample values includes detecting aberrant current flow in response to a continuous sequence of sampled values with magnitude differences greater than the threshold magnitude amount for a predetermined time duration.

14. The method of claim 10, wherein the detecting aberrant current flow between the conductive shield and anatomical tissue based upon the succession of sample values includes detecting aberrant current flow in response to detecting an occurrence of a predetermined number of sampled values with magnitude differences greater than the threshold magnitude amount during a predetermined time duration.

15. The method of claim 10, wherein the detecting aberrant current flow between the conductive shield and anatomical tissue based upon the succession of sample values includes detecting aberrant current flow in response to detecting an occurrence of a predetermined number of consecutive sampled values with magnitude differences greater than the threshold magnitude amount.

* * * * *